United States Patent [19]

Laurent et al.

[11] Patent Number: 5,439,902
[45] Date of Patent: Aug. 8, 1995

[54] 14α, 16α-ETHANO AND 14α,
16α-ETHENO-ESTRATRIENES

[75] Inventors: Henry Laurent; Peter Esperling; Walter Elger; Rolf Krattenmacher, all of Berlin, Germany

[73] Assignee: Schering Aktiengesellschaft, Berlin and Bergkamen, Germany

[21] Appl. No.: 140,053
[22] PCT Filed: Apr. 30, 1992
[86] PCT No.: PCT/EP92/00945
  § 371 Date: Mar. 18, 1994
  § 102(e) Date: Mar. 18, 1994
[87] PCT Pub. No.: WO92/19641
  PCT Pub. Date: Nov. 12, 1992

[30] Foreign Application Priority Data

Apr. 30, 1991 [DE] Germany .................. 41 14 635.2

[51] Int. Cl.⁶ .................... C07J 53/00; A61K 31/565
[52] U.S. Cl. .................... 514/179; 514/182; 552/510
[58] Field of Search ........ 514/179, 182; 552/629, 552/510

[56] References Cited

U.S. PATENT DOCUMENTS 4,407,753 10/1983 Groen .................. 552/629
4,789,671 12/1988 Bull et al. .

FOREIGN PATENT DOCUMENTS 0372665 6/1990 European Pat. Off. .
3808679 9/1989 Germany .
WO88/01275 2/1988 WIPO .

OTHER PUBLICATIONS

Bull et al. J Chem. Soc. Perkins Trans. 1, 19, 2545–2553.

Primary Examiner—Johann Richter
Assistant Examiner—Rebecca Cook
Attorney, Agent, or Firm—Millen, White, Zelano, & Branigan

[57] ABSTRACT

The new 14α,16α-ethano- and 14α,16α-etheno-estratrienes of general formula I,

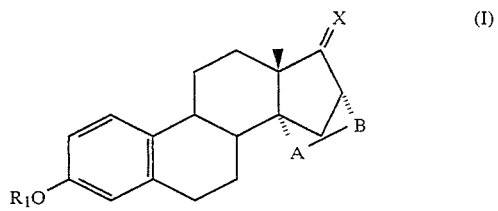

are described, in which
  A-B means a C-C single bond or C-C double bond,
  $R_1$ means a hydrogen atom, a methyl or acyl group with 1–12 carbon atoms and
  X means oxygen or

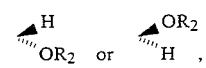

in which $R_2$ represents a hydrogen atom or an acyl group with 1–12 carbon atoms, and a process for their production. The new compounds are very strong estrogens and are suitable for the production of pharmaceutical agents.

7 Claims, 1 Drawing Sheet

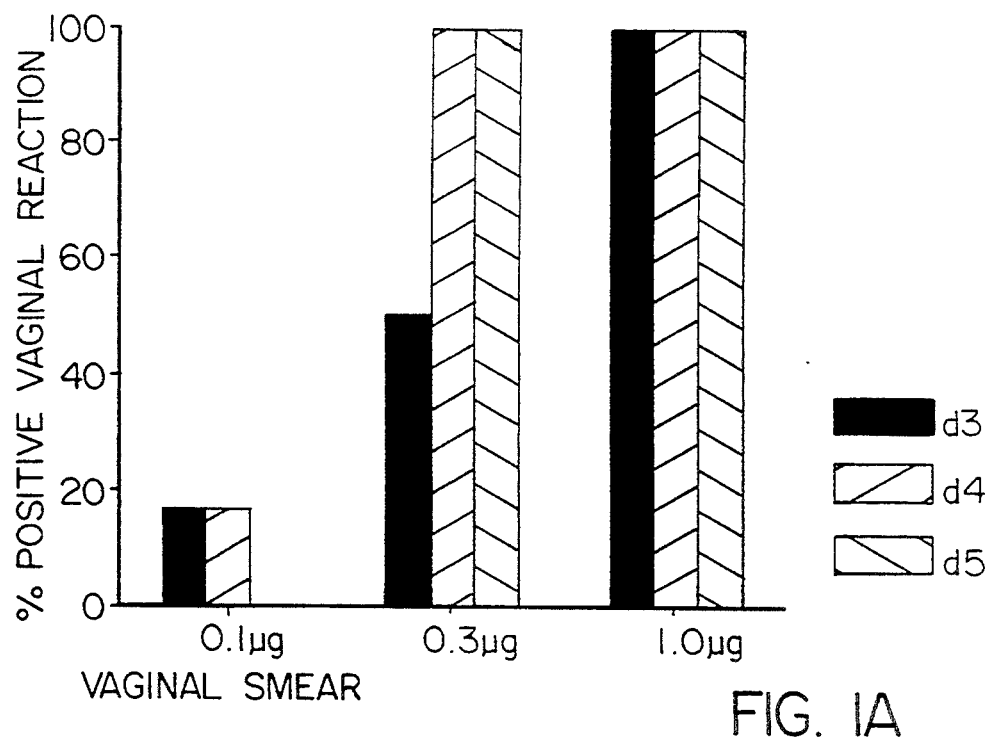
FIG. IA
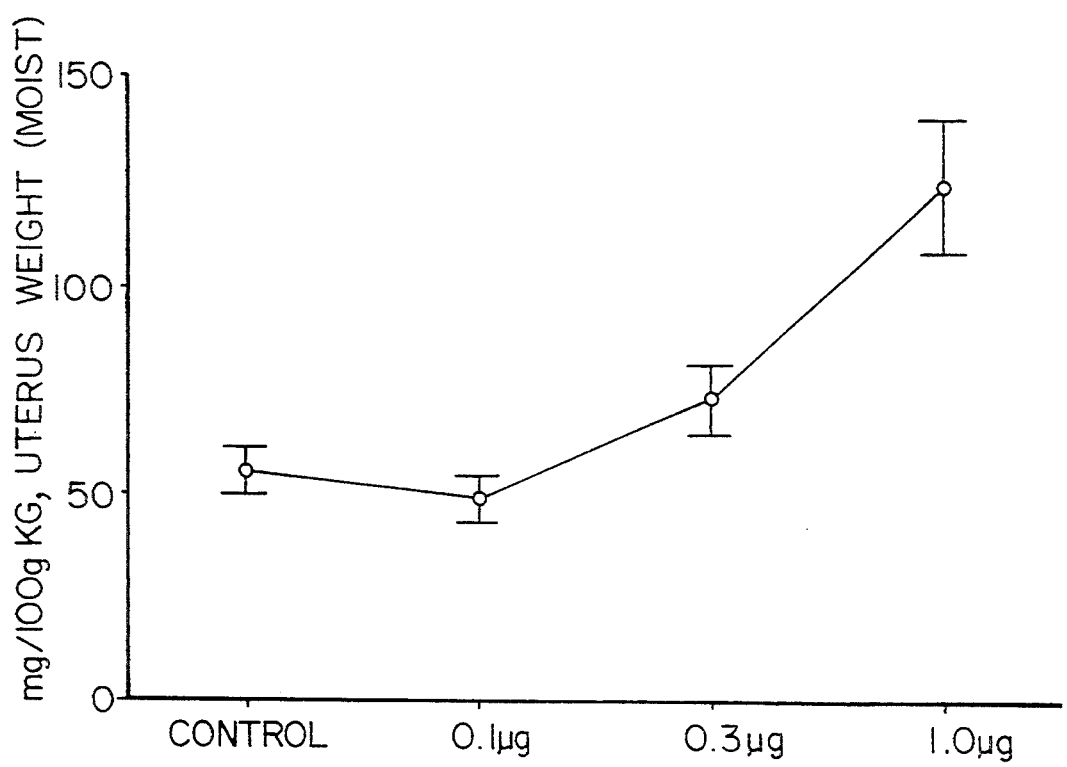
FIG. IB

14α,16α-ETHANO AND 14α, 16α-ETHENO-ESTRATRIENES

This application is a continuation of PCT/EP92/00945 filed Apr. 30, 1992.

The invention relates to 14α,16α-ethano- and 14α,16α-etheno-estratrienes of general formula I.

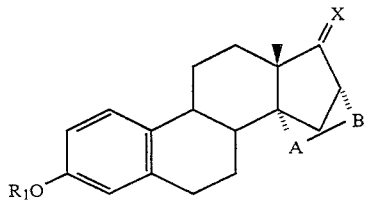

(I)

in which

A-B means a C-C single bond or C-C double bond, $R_1$ means a hydrogen atom, a methyl or acyl group with 1-12 carbon atoms and X means oxygen or

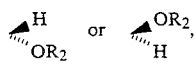

in which $R_2$ represents a hydrogen atom or an acyl group with 1-12 carbon atoms,
a process for their production, pharmaceutical preparations which contain these compounds, as well as their use for production of pharmaceutical agents.

As acyl groups $R_1$ and $R_2$, radicals of organic carboxylic acids with 1-12 carbon atoms are suitable. They are derived from aliphatic, cycloaliphatic, aliphatic-cycloaliphatic, cycloaliphatic-aliphatic and aromatic monocarboxylic acids with 1-12 carbon atoms. The number of carbon atoms in the ring varies from 3 to 5. As radicals $R_1$ and $R_2$, the acyl groups of acetic acid, propionic acid, butyric acid, isobutyric acid, pivalic acid, caproic acid, heptylic acid, caprylic acid, pelargonic acid, decanoic acid, undecanoic acid, dodecanoic acid, 3-cyclopentylpropionic acid and benzoic acid are preferred. The acyl radicals of carboxylic acids with 2-7 carbon atoms are especially preferred.

The new 14α,16α-ethano- and 14α,16α-etheno-estratrienes are very strong estrogens. In the Allen-Doisy test, the compounds of general formula I are even more active than estradiol, especially after oral administration. Surprising is above all the far better action of the 17α-hydroxy compounds according to the invention in comparison with the naturally occurring estradiol with 17α-hydroxy group (17α-estradiol) as can be seen from table 1.

TABLE 1

| | Compound | | |
|---|---|---|---|
| Verbindung | Allen-Doisy Test s.c. μg/animal/day [ED50] Allen-Doisy-Test s.c. μg/Tier/Tag [ED50] | Allen-Doisy Test p.o. μg/animal/day [ED50] Tabelle 1 Allen-Doisy-Test p.o. μg/Tier/Tag [ED50] | Estrogen-receptor test (KF) Estrogen-Rezeptor-Test [KF] |
| Estradiol | 0.2-0.5 | 50-100 | 1.0 |
| 17α-Estradiol | 100 | >1000 | 46.0 |
| 14α,16α-Ethano-estra-1,3,5(10)-trien-3,17α-diol | 0.1-0.3 | 3-10 | 0.5 |
| 14α,16α-Etheno-estra-1,3,5(10)-trien-3,17α-diol | | | 1.5 |
| 14α,16α-Ethano-estra-1,3,5(10)-trien-3,17β-diol | 0.1-0.3 | 1.0 | 1.0 |

In the Allen-Doisy test, an evaluation of vaginal smears in ovariectomized rats is performed on days 3–5 (d3-d5) after the one-time administration on day 1 (d1) of the test substance. The following cycle stages are distinguished:

1 = diestrus (leukocytes and nucleated epithelial cells),
2 = proestrus (nucleated epithelial cells),
3 = estrus (denucleated horny plaques),
4 = metestrus (denucleated horny plaques, leukocytes, epithelial cells).

After oral or subcutaneous administration, estrogenically active substances result in the proliferation of the vaginal epithelium and the hornification of superficial cell layers. As a threshold value, that amount of an estrogen is indicated in which 50% of the animals reach stage 3. Further, estrogens cause an increase of the uterus weight.

By the example of the 14α,16α-ethano-estra-1,3,5(10)-triene-3,17α-diol according to the invention, it is shown in FIG. 1 that after subcutaneous administration of only 0.3 μg in the rat, the threshold value is already exceeded.

BRIEF DESCRIPTION OF THE DRAWINGS

FIG. 1A shows the results of administration of various amounts of 14α, 16α-ethano-estra-1,3,5(10)-triene-3,17α-diol in the Allen-Doisy test on the rat, s.c., on the percentage of animals having a positive vaginal reaction, as indicated by vaginal smear. FIG. 1B shows the effect of administration of various amounts of this compound on the moist weight of the rat uterus.

The invention thus also relates to compounds of general formula I for use in the treatment of estrogen deficiency symptoms and for birth control in the female.

The compounds according to the invention can be formulated and used in the same way as ethinyl estradiol, which is the most used estrogen. They are processed with the additives, vehicles, and/or flavoring substances usual in galenic pharmaceutics according to methods known in the art to the usual forms of pharmaceutical agents. For oral administration, tablets, coated tablets, capsules, pills, suspensions or solutions are especially suitable. For parenteral administration, oily solutions, such as, for example, sesame oil or castor oil solutions are especially suitable, which optionally in addition can contain in addition a diluent, such as, for example, benzyl benzoate or benzyl alcohol.

The active ingredient concentration in the pharmaceutical compositions is a function of the form of administration and the field of use. Thus, for example, capsules or tablets for the treatment of estrogen deficiency symptoms can contain 0.001 to 0.05 mg of active ingredient, oily solutions for intramuscular injection per 1 ml about 0.01 to 0.1 mg of active ingredient and vaginal ointments about 0.1 to 10 mg per 100 ml of ointment. For contraception in the female, the estrogens according to the invention can be used in combination with gestagens. Tablets or coated tablets for daily intake of a tablet or a coated tablet preferably are to contain 0.003 to 0.05 mg of the estrogen according to the invention and 0.05 to 0.5 mg of a gestagen.

The compounds according to the invention can be used in estrogen deficiency symptoms of the female, such as, for example, amenorrhea, dysmenorrhea, sterility, endometritis, colpitis and menopausal symptoms and for prevention of osteoporosis. Further, the compounds can be used as estrogen components in hormonal contraceptives (single-phase and multiphase as well as multistage preparations). Further, they are suitable in connection with other active ingredients for use in hormone-carrying intra-uterine pessaries, implantable active ingredient vehicles as well as in transdermal administration systems.

The new 14α,16α-ethano and 14α,16α-etheno-estratrienes of general formula I

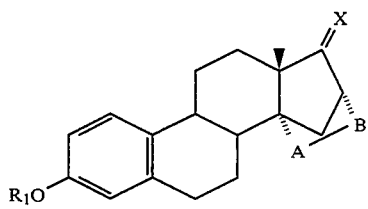

in which
A-B means a C-C single bond or C-C double bond,
$R_1$ means a hydrogen atom, a methyl or acyl group with 1–12 carbon atoms and
X means oxygen or

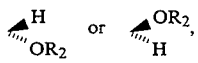

in which $R_2$ represents a hydrogen atom or an acyl group with 1–12 carbon atoms,
are produced by a 14α,17α-ethano- or 14α,17α-etheno-16β,17β-dihydroxy compound of general formula II,

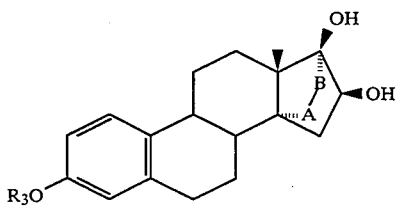

in which
A-B means a C-C single bond or a C-C double bond and
$R_3$ means a methyl or acyl group with 1–12 carbon atoms, being dehydrated with rearrangement to compounds of general formula I with X meaning oxygen, optionally then the 17-keto group being reduced to a 17α- or 17β-hydroxy group, optionally before or after the reduction of the 17-keto group, if A-B means a C-C double bond, the latter being catalytically hydrogenated, optionally the 3-methyl ether being cleaved or the 17-hydroxy group being esterified, optionally the 3-hydroxy group being partially esterified or the 3- and 17-hydroxy groups being simultaneously esterified and optionally a thus obtained 3,17-diacyloxy compound being selectively saponified to the 3-hydroxy-17-acyloxy compound.

The rearrangement of the 16β,17β-dihydroxy compounds of general formula II to 17-keto compounds of general formula I with X meaning oxygen takes place under dehydration conditions by an elimination with formation of a cation. According to a preferred embodiment, the dihydroxy compounds are treated with methanesulfonyl chloride in pyridine at temperatures of −10° to +10° C., optionally while adding sulfur dioxide. The rearrangement products are formed in surprisingly high yield, and acyloxy groups present in 3-position are partially saponified. 3-Hydroxy and 3-acyloxy compounds can be separated by simple chromatography. Depending on the finally desired compound, the partially saponified compounds can also be completely saponified or reacylated.

The optionally subsequent reduction of the 17-keto group to a 17α-hydroxy group is preferably performed with a mixed metal hydride. As a mixed metal hydride, sodium borohydride is especially suitable. As a solvent, alcohols, preferably ethanol, are used at reaction temperatures of 0° to 50° C.

If compounds of general formula I with a 17β-hydroxy group are to be produced, the reduction of the 17-keto group is performed radically preferably with an alkali or alkaline-earth metal, especially lithium in liquid ammonia. The optionally subsequent cleavage of a 3-methyl ether is performed according to the usual methods of steroid ether cleavage. Thus, the 3-methyl ether cleavage can preferably be performed with a Lewis acid in an inert solvent in boiling heat. As Lewis acids, for example, borontrifluoride etherate or diisobutyl aluminum hydride (DIBAH) are suitable. As solvent, benzene, toluene, tetrahydrofuran, dioxane, i.a., are suitable.

The saponification of the acyloxy groups can take place in a way known in the art. For example, the saponification is performed with bases in aqueous alcoholic solution, such as potassium hydroxide or potassium or calcium carbonate in aqueous-methanolic solution. For the optionally subsequent esterification of the phenolic and secondary hydroxy group, the process usually used in steroid chemistry for esterification is suitable. For example, the reaction with acetic acid or acetanhydride in the presense of strong acids, such as, for example, trifluoroacetic acid, perchloric acid or p-toluenesulfonic acid at room temperature or somewhat elevated temperature or the reaction with acetanhydride in the presence of amines, preferably pyridine, at about 20°–80° C., can be mentioned. The syntheses of the two possible semi-esters take place by partial esterification or partial saponification:

a) Starting from the 3,17-dihydroxy compounds, the 3-acyloxy-17-hydroxy compounds can be obtained by selective esterification of the phenolic hydroxy group. The reactions are achieved by reactions of the suitable acid anhydride in the presence of a heterocyclic nitrogen aromatic hydrocarbon, preferably pyridine. As reaction temperature, the range between room temperature and boiling temperature of the reaction mixture is suitable.

b) Starting from 3,17-diacyloxy compounds, the 3-hydroxy-17-acyloxy compounds can be obtained by selective saponification of the phenolic acyloxy group. The syntheses take place by reactions with an alkali carbonate or alkaline-earth carbonate, preferably potassium or calcium carbonate, in aqueous methanolic solution. As reaction temperature, the range between room temperature and boiling temperature of the reaction mixture is suitable.

Example 1

A solution of 920 mg of 3-acetoxy-14α,17α-ethano-estra-1,3,5(10)-triene-16β,17β-diol in 9.2 ml of pyridine is mixed under ice cooling with 1.42 ml of methanesulfonyl chloride, which contains 3% sulfur dioxide dissolved. The mixture is stirred for 20 minutes at 0° C. and then the reaction product is precipitated with water. The precipitate is isolated, washed with water, dried and chromatographed on 150 g of silica gel. 400 mg of 3-acetoxy-14α,16α-ethano-estra-1,3,5(10)-trien-17-one melting point 102° C., as well as 420 mg of 3-hydroxy-14α,16α-ethano-estra-1,3,5(10)-trien-17-one , melting point 265° C., are eluted with 2 l of hexane-ethyl acetate mixture (7:3).

Example 2

A solution of 420 mg of 3-hydroxy-14α,16α-ethano-estra-1,3,5(10)-trien-17-one in 30 ml of ethanol is mixed with 400 mg of sodium borohydride and stirred for 3 hours at room temperature under argon. The reaction mixture is diluted with ethyl acetate, the solution is washed with sodium chloride solution, dried on sodium sulfate and concentrated by evaporation in a vacuum. The residue is chromatographed on 75 g of silica gel with 1 l of hexane-ethyl acetate mixture (4:1). 270 mg is eluted, which, after the recrystallization from diethyl ether-hexane, yields 181 mg of 14α,16α-ethano-estra-1,3,5(10)-triene-3,17α-diol. Melting point 179° C.

Example 3

A solution of 500 mg of 3-methoxy-14α,17α-ethano-estra-1,3,5(10)-triene-16β,17β-diol in 5 ml of pyridine is mixed under ice cooling with 0.8 ml of methanesulfonyl chloride, which contains 3% sulfur dioxide dissolved. The mixture is stirred for 20 minutes at 0° C., then the reaction product is precipitated with water. The precipitate is isolated, washed with water, dried and chromatographed on 150 g of silica gel. With 2 l of pentanediethyl ether mixture (4:1), 450 mg of crystalline product, which is recrystallized from dichloromethane-hexane, is eluted. 370 mg of 3-methoxy-14α,16α-ethano-estra-1,3,5(10)-trien-17-one is obtained. Melting point 180° C.

Example 4

A solution of 300 mg of 3-methoxy-14α,16α-ethano-estra-1,3,5(10)-trien-17-one in 25 ml of ethanol is mixed with 300 mg of sodium borohydride and stirred for 4 hours at room temperature under argon. The reaction mixture is diluted with ethyl acetate, the solution is washed with sodium chloride solution, dried on sodium sulfate and concentrated by evaporation in a vacuum. 118 mg of 3-methoxy-14α,16α-ethano-estra-1,3,5(10)-trien-17α-ol is obtained from the residue by recrystallization from dichloromethane-hexane. Melting point 122° C.

Example 5

A solution of 140 mg of 14α,16α-ethano-estra-1,3,5(10)triene-3,17α-diol in 6.0 ml of pyridine is mixed with 3.0 ml of acetanhydride and stirred for 10 minutes at room temperature. The reaction mixture is mixed with 20 ml of water, the precipitated product is taken up in dichloromethane, the solution is dried and concentrated by evaporation in a vacuum. The residue is crystallized from diethyl ether-pentane and yields 108 mg of 3-acetoxy-14α,16α-ethano-estra-1,3,5(10)-trien-17α-ol. Melting point 153° C.

Example 6

A solution of 200 mg of 14α,16α-ethano-estra-1,3,5(10)-triene-3,17α-diol in 8.0 ml of pyridine is mixed with 4.0 ml of acetanhydride and stirred for 15 hours at room temperature. The reaction mixture is mixed with 30 ml of water, the precipitated product is taken up in dichloromethane, the solution is dried and concentrated by evaporation in a vacuum. The residue, crystallized from dichloromethane-hexane, yields 120 mg of 3,17α-diacetoxy-14α,16α-ethano-estra-1,3,5(10)-triene. Melting point 178° C.

Example 7

A solution of 60 mg of 3,17α-diacetoxy-14α,16α-ethano-estra-1,3,5(10)-triene in 10 ml of methanol is mixed with 1.0 ml of water as well as 60 mg of calcium carbonate and heated to boiling for 48 hours. Then, the reaction mixture is filtered and concentrated by evaporation in a vacuum. The crystalline residue of 50 mg is recrystallized from dichloromethane-diisopropyl ether. Yield 22 mg of 17α-acetoxy-14α,16α-ethano-estra-1,3,5(10)-trien-3-ol. Melting point 250° C.

Example 8

A solution of 200 mg of 3-acetoxy-14α,17α-etheno-estra-1,3,5(10)-triene-16β,17β-diol in 2.0 ml of pyridine is mixed under ice cooling with 0.3 ml of methanesulfonyl chloride, which contains 3% sulfur dioxide dissolved. The mixture is stirred for 15 minutes at 0° C. and then the reaction product is precipitated with water. The precipitate is isolated, washed with water, dried and chromatographed on silica gel. With a pentane-diethyl ether mixture (7:3), 60 mg is eluted, which, recrystallized from dichloromethane-diisopropyl ether, yields 64 mg of 3-acetoxy-14α,16α-etheno-estra-1,3,5(10)-trien-17-one. Melting point 127.8° C. Further, 260 mg is eluted, which, recrystallized from dichloromethane-methanol, yields 103 mg of 3-hydroxy-14α,16α-etheno-estra-1,3,5(10)-trien-17-one. Melting point 261.6° C.

Example 9

A solution of 210 mg of 3-hydroxy-14α,16α-etheno-estra-1,3,5(10)-trien-17-one in 30 ml of ethanol is mixed with 200 mg of sodium borohydride and stirred for 3 hours at room temperature under argon. The reaction mixture is diluted with ethyl acetate, the solution is washed with sodium chloride solution, dried on sodium sulfate and concentrated by evaporation in a vacuum. The residue of 190 mg is recrystallized from dichloromethane-methanol-diisopropyl ether, yields 95 mg of 14α,16α-etheno-estra-1,3,5(10)-triene-3,17α-diol. Melting point 249.9° C.

Example 10

A solution of 180 mg of 14α,17α-etheno-estra-1,3,5(10)-triene-3,17α-diol in a mixture of 10 ml of ethanol and 5 ml of tetrahydrofuran is mixed with 50 mg of palladium-carbon (10% Pd) and hydrogenated under standard pressure. After 40 minutes, it is filtered off from the catalyst, the filtrate is concentrated by evaporation in a vacuum, the residue is chromatographed on 100 g of silica gel with a hexane-ethyl acetate mixture (4:1). 121 mg of crystalline 14α,17β0 -ethano-estra-1,3,5(10)-triene-3,17α-diol is eluted. Melting point 174.2° C.

Example 11

150 ml of ammonia is condensed under cooling with solid carbon dioxide, 2.5 g of lithium cut into small sections is added, stirred for 15 minutes, and the deep blue solution is mixed drop by drop within 20 minutes with a solution of 2.4 g of 3-hydroxy-14α,16β0 -ethano-estra-1,3,5(10)-trien-17-one in 150 ml of anhydrous tetrahydrofuran and stirred for another 20 minutes. Then, a saturated ammonium chloride solution is carefully added, and the mixture is brought to room temperature. After the evaporation of the ammonia, it is mixed with 150 ml of water and extracted several times with dichloromethane-methanol (9:1). The combined extracts are dried on sodium sulfate and concentrated by evaporation in a vacuum. The residue is chromatographed on silica gel. 1.1 g of crystalline crude product is eluted with a dichloromethane-ethyl acetate mixture (75:25), which, after recrystallization of dichloromethane-diisopropyl ether, yields 496 mg of 14α,16α-ethano-estra-1,3,5(10)-triene-3,17β-diol. Melting point 148° C.

Production of the initial compounds

3,16β,17β-Triacetoxy-14α,17α-etheno-estra-1,3,5(10)-triene-16α-carbonitrile A solution of 3.0 g of estra-1,3,5(10),14,16-pentaene-3,17-diol diacetate in 10 ml of dichloromethane is mixed with 10 ml of 1-cyano-vinyl acetate and heated for 4 days in a closed tube to 140° C. The resinified reaction mixture is crushed in a mortar and treated with boiling acetone. After the decanting and evaporation of the solvent, 4.9 g of a residue remains, which is chromatographed on silica gel. It is eluted with a hexane-ethyl acetate mixture (7:3) and 3.78 g is obtained, which, recrystallized from dichloromethane-hexane, yields 3.28 g of 3,16β,17β-triacetoxy-14α,17α-etheno-estra-1,3,5(10)-triene-16α-carbonitrile. Melting point 162° C.

14α,17α-Etheno-estra-1,3,5(10)-triene-3,16β,17β-triol

A solution of 6.3 g of 3,16β,17β-triacetoxy-14α,17α-etheno-estra-1,3,5(10)-triene-16α-car bonitrile in 180 ml of anhydrous ethanol is mixed with 6.0 g of sodium borohydride and stirred for 15 hours at room temperature under argon. The reaction mixture is diluted with ethyl acetate, the solution is washed with water, dried on sodium sulfate and concentrated by evaporation in a vacuum. The residue is chromatographed on 200 g of silica gel with 3 l of dichloromethane-methanol mixture (95:5). 3.21 g of a crystalline substance is eluted. After the recrystallization of diisopropyl ether-methanol, 2.38 g of 14α,17α-etheno-estra-1,3,5(10)-triene-3,16β,17β-triol is obtained. Melting point 227° C.

14α,17α-Ethano-estra-1,3,5(10)-triene-3,16β,17β-triol

A solution of 110 mg of 14α,17α-etheno-estra-1,3,5(10)-triene-3,16β,17β-triol in a mixture of 6 ml of ethanol and 1.5 ml of tetrahydrofuran is mixed with 20 mg of palladium-carbon (10% Pd) and hydrogenated under standard pressure. After absorption of 10.5 ml of hydrogen (calculated 8.7 ml) within 30 minutes, the palladium catalyst is filtered off. The filtrate is concentrated by evaporation in a vacuum, and the residue is recrystallized from a methanol-diisopropyl ether mixture. Yield: 105 mg of 14α,17α-ethano-estra-1,3,5(10)-triene-3,16β,17β-triol. Melting point 230° C.

3-Acetoxy-14α,17α-etheno-estra-1,3,5(10)-triene-16β,17β-diol

A solution of 2.36 g of 14α,17α-etheno-estra-1,3,5(10)-triene-3,16β,17β-triol in a mixture of 20 ml of pyridine and 5 ml of acetanhydride is held at room temperature for 20 minutes. The reaction solution is stirred in ice/common salt solution, the precipitated precipitate is filtered off, washed with water, dried and chromatographed on 125 g of silica gel. With 5 l of hexane-ethyl acetate mixture (7:3), 1.79 g of crystalline 3-acetoxy-14α,17α-etheno-estra-1,3,5(10)-tr iene-16β,17β-diol is eluted. Melting point 202° C.

3-Acetoxy-14α,17α-ethano-estra-1,3,5(10)-triene-16β,17β-diol

A solution of 1.0 g of 3-acetoxy-14α,17α-etheno-estra-1,3,5(10)-triene-16β,17β-diol in a mixture of 60 ml of ethanol and 25 ml of tetrahydrofuran is mixed with 250 mg of palladium-carbon (10% Pd) and hydrogenated under standard pressure. After absorption of 85 ml of hydrogen (calculated 68 ml) within 5 minutes, it is filtered off from the catalyst. The filtrate is concentrated by evaporation in a vacuum and the residue is recrystallized from dichloromethane-diisopropyl ether. 571 mg of 3-acetoxy-14α,17α-ethano-estra-1,3,5(10)-triene-16β,17β-diol is obtained. Melting point 193° C.

16β,17β-Diacetoxy-3-methoxy-14α,17α-etheno-estra-1,3,5(10)-triene-16α-carbonitrile A solution of 2.0 g of 3-methoxy-estra-1,3,5(10),14,16-pentaen-17-ol-acetate in 20 ml of benzene is mixed with 4.6 ml of 1-cyano-vinyl acetate and heated in a pressure vessel for 4 days to 100° C. The reaction mixture is chromatographed on 400 g of silica gel with ethyl acetate-hexane (1:1) and yields, after recrystallization from diisopropyl ether-hexane, 1.9 g of 16β,17β-diacetoxy-3-methoxy-14α,17α-etheno-estra-1,3,5(10)-triene-16α-carbonitrile. Melting point 144° C.

3-Methoxy-14α,17α-etheno-estra-1,3,5(10)-triene-16β,17β-diol

A solution of 400 mg of 16β,17β-diacetoxy-3-methoxy-14α,17α-etheno-estra-1,3,5(10)-triene-16α-carbonitrile in 30 ml of anhydrous ethanol is mixed with 300 mg of sodium borohydride and stirred for 3 hours at room temperature under argon. The reaction mixture is diluted with ethyl acetate, the solution is washed with water, dried on sodium sulfate and concentrated by evaporation in a vacuum. The residue is chromatographed on 100 g of silica gel with a hexane-ethyl acetate mixture (0–20% ethyl acetate). 151 mg is eluted, which, after the recrystallization of dichloromethane-methanol, yields 111 mg of 3-methoxy-14α,17α-ethenoestra-1,3,5(10)-triene-16β,17 β-diol Melting point 167° C.

3-Methoxy-14α,17α-ethano-estra-1,3,5(10)-triene-16β,17β-diol

A solution of 700 mg of 3-methoxy-14α,17α-etheno-estra-1,3,5(10)-triene-16β,17β-diol in a mixture of 30 ml of ethanol and 15 ml of tetrahydrofuran is mixed with 200 mg of palladium-carbon (10% Pd) and hydrogenated under standard pressure. After absorption of 57 ml of hydrogen (calculated 51 ml) within 40 minutes, it is filtered off from the catalyst. The filtrate is concentrated by evaporation in a vacuum, the residue is chromatographed on 100 g of silica gel with a hexane-ethyl acetate mixture (7:3) and the eluted substance of 540 mg of dichloromethane-diisopropyl ether is recrystallized. 268 mg of 3-methoxy-14α,17α-ethano-estra-1,3,5(10)-triene-16β,17β-diol is obtained. Melting point 172° C.

We claim:

1. A 14α,16α-Ethano- or 14α,16α-etheno-estratriene of formula I,

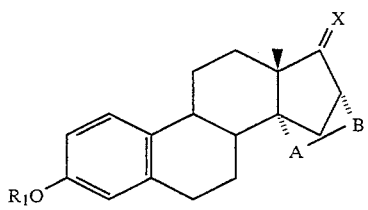

(I)

wherein
A-B is a C-C single bond or C-C double bond,
R₁ is a hydrogen atom, a methyl or acyl group with 1-12 carbon atoms and
X is oxygen or

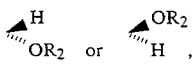

wherein R₂ represents a hydrogen atom or an acyl-group with 1-12 carbon atoms.

2. A compound of claim 1, which is:
3-Acetoxy-14α,16α-ethano-estra-1,3,5(10)-trien-17-one,
3-acetoxy-14α,16α-etheno-estra-1,3,5(10)-trien-17-one,
3-hydroxy-14α,16α-ethano-estra-1,3,5(10)-trien-17-one,
3-hydroxy-14α,16α-etheno-estra-1,3,5(10)-trien-17-one,
14α,16α-ethano-estra-1,3,5(10)-triene-3,17α-diol,
14α,16α-etheno-estra-1,3,5(10)-triene-3,17α-diol,
14α,16α-ethano-estra-1,3,5(10)-triene-3,17β-diol,
14α,16α-etheno-estra-1,3,5(10)-triene-3,17β-diol,
3-methoxy-14α,16α-ethano-estra-1,3,5(10)-trien-17-one,
3-methoxy-14α,16α-etheno-estra-1,3,5(10)-trien-17-one,
3-methoxy-14α,16α-ethano-estra-1,3,5(10)-trien-17α-ol,
3-methoxy-14α,16α-etheno-estra-1,3,5(10)-trien-17α-ol,
3-methoxy-14α,16α-ethano-estra-1,3,5(10)-trien-17β-ol,
3-methoxy-14α,16α-etheno-estra-1,3,5(10)-trien-17β-ol,
3-acetoxy-14α,16α-ethano-estra-1,3,5(10)-trien-17α-ol,
3-acetoxy-14α,16α-etheno-estra-1,3,5(10)-trien-17α-ol,
3-acetoxy-14α,16α-ethano-estra-1,3,5(10)-trien-17β-ol,
3-acetoxy-14α,16α-etheno-estra-1,3,5(10)-trien-17β-ol,
3,17α-diacetoxy-14α,16α-ethano-estra-1,3,5(10)-triene,
3,17α-diacetoxy-14α,16α-etheno-estra-1,3,5(10)-triene,
3,17β-diacetoxy-14α,16α-ethano-estra-1,3,5(10)-triene,
3,17β-diacetoxy-14α,16α-etheno-estra-1,3,5(10)-triene,
17α-acetoxy-14α,16α-ethano-estra-1,3,5(10)-trien-3-ol,
17α-acetoxy-14α,16α-etheno-estra-1,3,5(10)-trien-3-ol,
17β-acetoxy-14α,16α-ethano-estra-1,3,5(10)-trien-3-ol or
17β-acetoxy-14α,16α-etheno-estra-1,3,5(10)-trien-3-ol.

3. A pharmaceutical preparation comprising a compound of claim 1 and a pharmacologically compatible vehicle.

4. A method of birth control in a female, comprising administering to a female in need of such treatment an effective amount of a compound of claim 1.

5. A process for the production of a 14α,16α-ethano- or 14α,16α-etheno-estratriene of formula I,

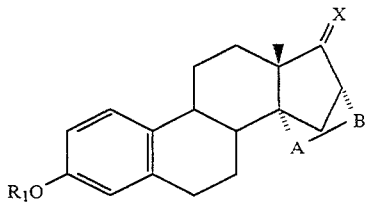

(I)

wherein
A-B is a C-C single bond or C-C double bond,
R₁ is a hydrogen atom, a methyl or acyl group with 1-12 carbon atoms and
X is oxygen or

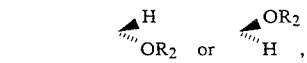

wherein R₂ represents a hydrogen atom or an acyl group with 1-12 carbon atoms, comprising dehydrating, with rearrangement, a 14α,17α-ethano- or 14α,17α-etheno-16β,17β-dihydroxy compound of formula II,

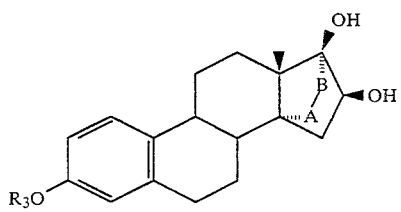

(II)

wherein

A-B is a C-C single bond or a C-C double bond and
$R_3$ is a methyl or acyl group with 1–12 carbon atoms,
to a compound of formula I wherein X is oxygen,
optionally reducing the 17-keto group to the 17α- or 17β-hydroxy group,
optionally before or after the reduction of the 17-keto group, wherein A-B is a C-C double bond, catalytically hydrogenating said double bond,
optionally cleaving the 3-methyl ether or esterifying the 17-hydroxy group,
optionally partially esterifying the 3-hydroxy group or simultaneously esterifying the 3- and 17-hydroxy groups and
optionally selectively saponifying a thus obtained 3,17-diacyloxy compound to produce the 3-hydroxy-17-acyloxy compound.

6. A pharmaceutical preparation, comprising a compound of claim 2 and a pharmacologically compatible vehicle.

7. A method of birth control in a female, comprising administering to a female in need of such treatment an effective amount of a compound of claim 2.

* * * * *